United States Patent [19]
Bonnet et al.

[11] Patent Number: 5,024,212
[45] Date of Patent: Jun. 18, 1991

[54] ENDOSCOPE/RESECTOSCOPE AND SHIELD THEREFOR

[75] Inventors: Ludwig Bonnet, Knittlingen; Ulrich Wetterauer, Freiburg, both of Fed. Rep. of Germany

[73] Assignee: Richard Wolf GmbH, Knittlingen, Fed. Rep. of Germany

[21] Appl. No.: 514,908

[22] Filed: Apr. 26, 1990

[30] Foreign Application Priority Data

Jun. 8, 1989 [DE] Fed. Rep. of Germany ....... 3918719

[51] Int. Cl.⁵ .................................................. A61B 1/00
[52] U.S. Cl. ............................................ 128/4; 606/46
[58] Field of Search ...................... 128/4, 6; 606/46

[56] References Cited

U.S. PATENT DOCUMENTS

| | | | |
|---|---|---|---|
| 1,679,950 | 8/1928 | Stern | 606/46 |
| 3,144,020 | 8/1964 | Zingale | 606/46 X |
| 4,422,852 | 12/1983 | Mathias | 40/331 X |
| 4,430,996 | 2/1984 | Bonnet | 606/46 |
| 4,834,068 | 5/1989 | Gottesman | 128/4 |
| 4,848,322 | 7/1989 | Dash et al. | 128/4 |

Primary Examiner—William H. Grieb
Attorney, Agent, or Firm—Panitch, Schwarze, Jacobs & Nadel

[57] ABSTRACT

An endoscope, in particular a resectoscope, for excising tissue, having a barrel insertable into a body cavity for feeding in and draining out an irrigating liquid and for carrying a working element which can be actuated from the proximal end of the endoscope and whose field of activity can be monitored visually through an endoscope telescope positioned at the proximal end of the endoscope, in which to protect a surgeon, a protective shield can be releasably secured on a lengthwise segment of the endoscope, namely on a lengthwise segment comprising those segments of the working element and of the endoscope telescope which project proximally from the barrel of the endoscope.

8 Claims, 1 Drawing Sheet

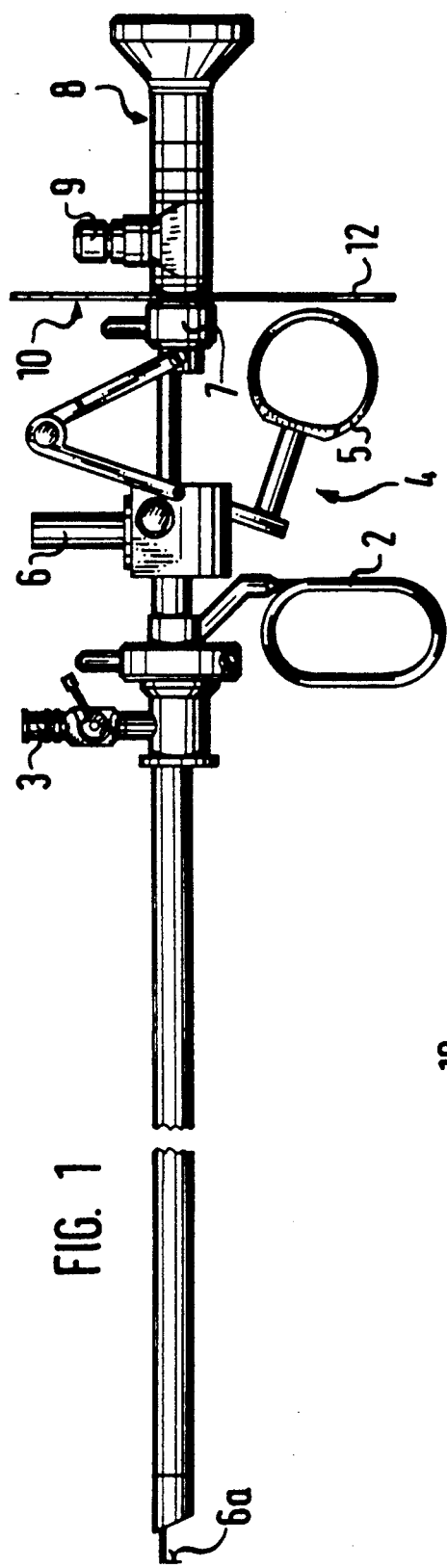
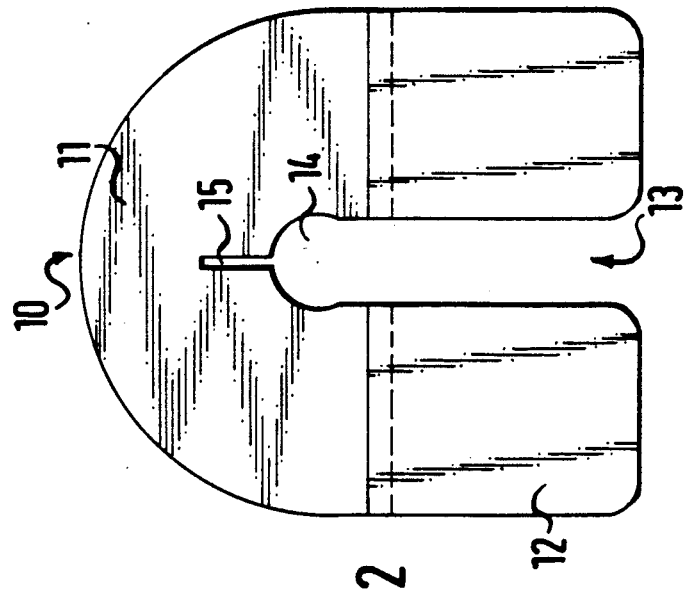
FIG. 1
FIG. 3
FIG. 2

ENDOSCOPE/RESECTOSCOPE AND SHIELD THEREFOR

BACKGROUND OF THE INVENTION (a) Field of the Invention

This invention relates to an endoscope, in particular a resectoscope, for excising tissue, in prostate resection for example, having a barrel which is insertable into a body cavity, for conveying irrigating liquid and for carrying a working element which can be actuated from the proximal end of the endoscope and whose field of activity can be monitored visually through an endoscope telescope connected to the proximal end of the endoscope.

(b) Description of the Prior Art

With resectoscopes of this kind, quite large amounts of irrigating liquid are usually needed, particularly for flushing out the pieces of tissue which have been excised. The procedure adopted for this is, once a given amount of tissue has been excised, for the working element to be withdrawn from the barrel of the endoscope which has been inserted into the body cavity, so that the excised pieces of tissue and the irrigating liquid can then be extracted from the body cavity through the relatively large cross-section of the barrel.

When manipulating the resectoscope, there is usually no way of preventing the irrigating liquid from getting onto the face of the operator who is carrying out the endoscopic operation and following it through the telescope, because at the proximal end of the resectoscope, the liquid is allowed to drain away freely into a suitable collecting container. Not only does the operator find this sort of contact with the irrigating liquid unpleasant and very much of a nuisance, but there is also a major risk of AIDS and/or hepatitis viruses being transmitted by the contact. The viruses can then find their way into the blood through the mucous membrances of the eyes, nose and mouth and produce the relevant disease.

To prevent infection of this kind or to reduce the risk of infection, transparent protective masks are worn over the face. However, because they are not very comfortable for the wearer and because air does not circulate well behind them, face masks of this kind are a very great nuisance to wear. In the same way, eye-shields and mouth guards help to reduce the risk of infection but are equally unable to rule it out completely. Another reason why ancillaries of this kind are disliked is because they are found to have a distracting influence when the operation is being performed.

The main object of the present invention is to provide the operator performing an endoscopic operation with reliable protection against the risk of infection from irrigating liquid which is splashed about, without the need for him or her to put on ancillaries which are an encumbrance or create a nuisance of some other kind.

SUMMARY OF THE INVENTION

To this end, the present invention consists in an endoscope, in particular a resectoscope, for excising tissue, having a barrel which is insertable into a body cavity, for feeding in and draining out an irrigating liquid and for carrying a working element which can be actuated from the proximal end of the endoscope and whose field of activity can be monitored visually through an endoscope, characterised in that a protective shield can be releasably secured on a lengthwise segment of the endoscope, said lengthwise segment being formed by those segments of the working element and of the endoscope telescope which project proximally from the barrel of the endoscope.

By means of the invention, the advantages thereby achievable lie in particular in the facts that the protective shield and the resectoscope form a single unit and the face of the operator who is following the operation through the endoscopic telescope is screened off directly from the field of activity of the working element.

The protective shield according to the invention can be very simply fitted into place by slotting it on if it is U-shaped in configuration, with the two legs of the U being created by a cutout whose width is substantially the same as the diameter of that part of the endoscope or telescope which carries the shield. This being the case, the shield can be provided with a particularly secure hold by giving it a central opening whose diameter is slightly smaller than the diameter of the part of the instrument or telescope which carries the shield, the opening communicating with a cutout whose width is smaller than the diameter of the said opening.

In a refinement of the invention that part of the protective shield which surrounds the central opening is made from a rigid, elastically deformable material and the parts adjoining the cutout are made of the same material or of a soft and elastic material, each part preferably being transparent in nature. The effect of forming the legs which connect up with the rigid part from a soft and elastic material is a beneficial one when the resectoscope is being handled because the legs rest tightly against the surface of the operator's hand and follow every movement it makes.

A slot which communicates with the top region of the opening allows the cutout and the opening to be deformed resiliently, within limits, thus enabling the shield to be safely and securely held on the part of the element or on the telescope by the spring loading resulting from the deformation.

In a further refinement of the invention, the protective shield may have a coupling member in the region of the opening so that it can, for example, be positioned or locked between the telescope and the working element.

BRIEF DESCRIPTION OF THE DRAWINGS

In order that the invention may be more readily understood, embodiments thereof will now described, by way of example, with reference to the accompanying drawings, in which:

FIG. 1 shows a resectoscope with a protective shield constructed according to the invention, FIG. 2 is an enlarged front elevation of the protective shield shown in FIG. 1, and FIG. 3 is a side elevation of the protective shield shown in FIG. 2.

DESCRIPTION OF THE PREFERRED EMBODIMENTS

Referring to the drawings, FIG. 1 shows an endoscope in the form of a resectoscope of the kind used in practice and having proximal and distal ends. The resectoscope comprises, in essence, a barrel 1, which has a handle 2 and an infeed nozzle 3 for irrigating liquid. The barrel 1 of the resectoscope is used to receive and have passed through it both a known working element, 4, which has a thumb-ring 5 and a connector 6 for supplying high frequency current to a resection loop 6a, and a known endoscope telescope 8 which has a light-guide connector 9 and which can be releasably connected to the working element 4 by means of a proximal union 7.

In the embodiment shown, the protective shield 10 according to the invention is preferably positioned between the light-guide connector 9 on the telescope 8 and the union 7. As can be seen from FIG. 2, the protective shield 10 has a bridging portion 11 made from a rigid material, non-releasably connected to which are parts 12 of an elastic nature, thus giving the protective shield 10 a U-shape, with the parts 12 forming the legs of the U, which define a cutout 13. In the central region of the protective shield 10 is an opening 14 communicating with the cutout 13. At the upper end of the opening 14 is provided a radial stress-relieving slot 15 communicating with the opening, the size selected for which slot is such that the deformation to which the protective shield 10 is subjected when it is being slotted into position remains within the elastic range, as a result of which the restorative force resulting therefrom causes the protective shield 10 to be safely and securely held in place on the appropriate part of the instrument.

In another embodiment of the protective shield 10 according to the invention, which is not shown, it is conceivable for fasteners to be provided to secure the shield releasably in position on the working element 4 or on the endoscope telescope 8, said fasteners allowing a frictional or positive connection to be made. It is also possible for a coupling member to be provided. Compared with the embodiment of the protective shield 10 which is described above, coupling members of this kind have the advantage that they provide a better connection between the respective parts of the instrument.

To optimise the shielding action, it is also conceivable for the size or shape of the protective shield 10 to be adjusted to suit. For this purpose, it may even be curved towards the patient.

It should be appreciated that the invention is not limited to the embodiments herein described but includes all modifications and variations falling within its scope.

We claim:

1. An endoscope, in particular a resectoscope for excising tissue, said endoscope having proximal and distal ends and comprising a barrel which is insertable into a body cavity, for feeding in and draining out an irrigating liquid and for carrying a working element which is actuatable from the proximal end of the endoscope and which has a field of activity that can be monitored visually through an endoscope telescope positioned at the proximal end of the endoscope, wherein a protective shield is releasably secured on a lengthwise segment of the endoscope, said lengthwise segment comprising those segments of the working element and of the endoscope telescope which project proximally from the barrel of the endoscope, the protective shield having a U-shaped configuration, with the two legs of the U being created by a cutout whose width is less than the diameter of at least one of the working element and telescope which carries the protective shield.

2. An endoscope according to claim 1, wherein the protective shield has a central region defining an opening which is slightly smaller than the diameter of at least one of the working element and endoscope telescope which carries the said shield, with the opening communicating with the said cutout.

3. An endoscope according to claim 2, said shield having slot which communicates with the said opening in the protective shield thereby to impart elasticity to a bridging portion connecting the two legs.

4. An endoscope according to claim 1, wherein the protective shield is releasably secured between a union forming part of the working element and a light-guide connector forming part of the endoscope telescope.

5. An endoscope, in particular a resectoscope, for excising tissue, said endoscope having proximal and distal ends and comprising a barrel which is insertable into a body cavity, for feeding in and draining out an irrigating liquid and for carrying a working element which is actuatable from the proximal end of the endoscope and which has a field of activity that can be monitored visually through an endoscope telescope positioned at the proximal end of the endoscope, wherein a protective shield is releasably secured on a lengthwise segment of the endoscope, said lengthwise segment comprising those segments of the working element and of the endoscope telescope which project proximally from the bridging portion and two legs interconnected by the bridging portion, said legs being of soft and elastic plastic material and wherein all parts of the shield are transparent.

6. An endoscope according to claim 5, wherein the protective shield has a central region defining an opening which is slightly smaller than the diameter of at least one of the working element and endoscope telescope which carries said shield.

7. An endoscope according to claim 6, said shield having a slot which communicates with said opening in said protective shield thereby to impart elasticity to said bridging portion connecting said two legs.

8. An endoscope according to claim 5, wherein said protective shield is releasably secured between a union forming part of the working element and a light-guide connector forming part of the endoscope telescope.

* * * * *